United States Patent
Cotsarelis et al.

(10) Patent No.: US 12,201,625 B2
(45) Date of Patent: Jan. 21, 2025

(54) SINGLE NUCLEOTIDE POLYMORPHIC ALLELES OF HUMAN DP-2 GENE FOR DETECTION OF SUSCEPTIBILITY TO HAIR GROWTH INHIBITION BY PGD2

(71) Applicant: THE TRUSTEES OF THE UNIVERSITY OF PENNSYLVANIA, Philadelphia, PA (US)

(72) Inventors: George Cotsarelis, Berwyn, PA (US); Ying Zheng, West Chester, PA (US); Jen-Chih Hsieh, South Setauket, NY (US); David Collins, Philadelphia, PA (US); Joan O'Brien, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 194 days.

(21) Appl. No.: 15/748,641

(22) PCT Filed: Jul. 28, 2016

(86) PCT No.: PCT/US2016/044457
§ 371 (c)(1),
(2) Date: Jan. 29, 2018

(87) PCT Pub. No.: WO2017/019858
PCT Pub. Date: Feb. 2, 2017

(65) Prior Publication Data
US 2020/0078351 A1    Mar. 12, 2020

Related U.S. Application Data
(60) Provisional application No. 62/198,888, filed on Jul. 30, 2015.

(51) Int. Cl.
*A61K 31/473* (2006.01)
*A61K 9/00* (2006.01)
(Continued)

(52) U.S. Cl.
CPC .......... *A61K 31/473* (2013.01); *A61K 9/0014* (2013.01); *A61K 9/0053* (2013.01);
(Continued)

(58) Field of Classification Search
CPC ........ A61K 38/00; A61K 8/368; A61K 8/492; A61K 8/4926; A61K 8/69; A61K 9/0014;
(Continued)

(56) References Cited

U.S. PATENT DOCUMENTS

| | | | |
|---|---|---|---|
| 9,889,082 B2 * | 2/2018 | Cotsarelis | .......... A61K 31/7088 |
| 10,849,841 B2 * | 12/2020 | Cotsarelis | .............. A61Q 19/00 |
| 2015/0072963 A1 | 3/2015 | Cotsarelis et al. | |

FOREIGN PATENT DOCUMENTS

| | | | |
|---|---|---|---|
| WO | WO 2003/018835 A2 | 3/2003 | |
| WO | WO-03018835 A2 * | 3/2003 | ........... C12Q 1/6827 |

(Continued)

OTHER PUBLICATIONS

Bain (Pharmacodynamics, Pharmacokinetics, and Safety of AM211: A Novel and Potent Antagonist of the Prostaglandin D2 Receptor Type 2, Journal of Clinical Pharmacology, 2012;52:1482-1493).*
(Continued)

*Primary Examiner* — Jeffrey S Lundgren
*Assistant Examiner* — Anthony Joseph Seitz
(74) *Attorney, Agent, or Firm* — Mark S. Cohen; PEARL COHEN ZEDEK LATZER BARATZ LLP

(57) ABSTRACT

DP-2 antagonists reversed $PGD_2$-mediated human hair growth inhibition in a dose-dependent manner in vitro by reducing $PGD_2$-triggered apoptosis and maintaining proliferation of keratinocytes. Hair follicles from approximately half of the alopecia patients exhibited little susceptibility to $PGD_2$'s effect in vitro. SNPs in the human DP-2 gene were identified that are associated with hair growth inhibition by $PGD_2$. These findings underscore the role of DP-2 in regu-
(Continued)

lating hair growth and indicate that DP-2 can be an effective approach in preventing and/or treating androgenetic alopecia in patients sensitive to PGD$_2$. Furthermore, the SNPs identified here can be used to identify patients who will benefit from treatment.

9 Claims, 4 Drawing Sheets

(51) Int. Cl.
*A61K 31/192* (2006.01)
*A61K 31/404* (2006.01)
*A61K 31/437* (2006.01)
*A61K 31/47* (2006.01)
*A61K 31/506* (2006.01)
*A61P 17/14* (2006.01)
*C12Q 1/6883* (2018.01)

(52) U.S. Cl.
CPC .......... *A61K 31/192* (2013.01); *A61K 31/404* (2013.01); *A61K 31/437* (2013.01); *A61K 31/47* (2013.01); *A61K 31/506* (2013.01); *A61P 17/14* (2018.01); *C12Q 1/6883* (2013.01); *C12Q 2600/106* (2013.01); *C12Q 2600/156* (2013.01)

(58) Field of Classification Search
CPC ........ A61K 9/0053; A61P 17/14; A61P 17/00; A61P 43/00; A61Q 7/00; C12Q 1/68; C12Q 1/6883; C12Q 2600/106; C12Q 2600/156; G03F 7/038; G03F 7/0382; G03F 7/085; G03F 7/16; G03F 7/20; G03F 7/30
See application file for complete search history.

(56) References Cited

FOREIGN PATENT DOCUMENTS

| WO | WO 2007/149312 | 12/2007 | |
|---|---|---|---|
| WO | WO-2009114741 A1 * | 9/2009 | .............. A61P 17/00 |
| WO | WO 2013/142295 | 9/2013 | |
| WO | WO-2013142295 A1 * | 9/2013 | ......... A61B 17/3205 |

OTHER PUBLICATIONS

Journal of Clinical Pharmacology (2012) 52:1482-93 (Year: 2012).*
Allergy (2012) 67:1357-64 (Year: 2012).*
Campos Alberto, E et al. The Single Nucleotide Polymorphism CRTh2 rs533116 is Associated with Allergic Asthma and Increased Expression of CRTh2. Allergy. Nov. 2012, vol. 67. No. 11; pp. 1357-1364; abstract; 001: 10.1111/all.12003.
Cameron, L et al.) Genetic Variation in CRTh2 Influences Development of Allergic Phenotypes. Allergy. Oct. 2009, vol. 64, No. 10; pp. 1478-1485; Figure 2A; DOI: 10.1111/j.1398-9995.2009. 02053.x.
European Search Report from European Patent Application No. 16831347.6 dated Mar. 26, 2019.
Garza et al., "Prostaglandin D2 Inhibits Hair Growth and is Elevated in Bald Cap Scalp of Men with Androgenetic Alopecia". Science Translation Medicine, vol. 4, No. 126, Mar. 21, 2012 pp. 126ra34-126ra34.
International Search Report and Written Opinion from PCT Patent Application No. PCT/US2016/044457 dated Feb. 8, 2018.

* cited by examiner

SINGLE NUCLEOTIDE POLYMORPHIC ALLELES OF HUMAN DP-2 GENE FOR DETECTION OF SUSCEPTIBILITY TO HAIR GROWTH INHIBITION BY PGD2

FIELD OF THE INVENTION

The invention relates to compositions and methods for regulating hair growth. Specifically, the invention relates to identifying subjects, such as those with androgenetic alopecia or baldness or hair loss, susceptible to hair growth inhibition by prostaglandin D2 ($PGD_2$) and responsive to $PGD_2$ receptor, DP-2 (aka CRTH2 or GPR44) antagonists to stimulate hair growth.

BACKGROUND OF THE INVENTION

Eighty percent of Caucasian men experience some degree of androgenetic alopecia (AGA) before age 70. Testosterone is necessary for AGA to develop, and a genetic susceptibility locus in the androgen receptor is present in a minority of men with AGA; however, additional factors contributing to this disorder remain unknown. Studies on AGA have the potential to yield insights into other androgen-mediated diseases, such as benign prostatic hypertrophy and prostate cancer. Current legitimate treatments for AGA include finasteride, minoxidil, and hair transplantation. Finasteride inhibits 5-α reductase 2 (SRD5A2), which converts testosterone to a more potent androgen, dihydrotestosterone. The active targets of minoxidil in AGA therapy have not been conclusively identified.

In AGA, large "terminal" hair follicles forming thick hair shafts miniaturize over time to small follicles that generate microscopic effete hairs. Follicle miniaturization is accompanied by a decrease in the duration of the growing phase of the follicle (anagen), which normally lasts several years to produce hair more than 1 m long, but which decreases to only days or weeks in AGA. This results in an increase in the percentage of resting (telogen) hair follicles containing microscopic hairs in bald scalp.

In addition to these intrinsic changes to the hair follicle, infiltrating lymphocytes and mast cells have been identified around the miniaturizing follicle, especially in the area of the stem cell-rich bulge area. Sebaceous glands, which attach to each follicle, hypertrophy in bald scalp. In balding scalp, the number of hair follicle stem cells remains intact, whereas the number of more actively proliferating progenitor cells markedly decreases. This indicates that balding scalp either lacks an activator or has an inhibitor of hair follicle growth.

Prostaglandin $D_2$ ($PGD_2$) and its synthesizing enzyme, $PGD_2$ synthase, are present at higher levels in balding versus non-balding scalp in men with androgenetic alopecia. In a mouse model, $PGD_2$ inhibited hair growth via CRTH2/DP-2, one of two $PGD_2$ receptors, indicating that DP-2 is the key receptor mediating the hair growth inhibitory activity of $PGD_2$ in human follicles (Garza et al. (2012) *Sci. Transl. Med.* 4, 126ra34).

Accordingly, there exists a need for compositions and methods for stimulating hair growth, as well as to identify who would likely to be responsive to them.

SUMMARY OF THE INVENTION

In one aspect, provided herein are methods for stimulating hair growth in a subject, the methods comprising: administering to said subject an effective amount of a DP-2 antagonist.

In another aspect, provided herein are methods of identifying whether a subject having androgenetic alopecia, baldness or hair loss is likely to be responsive to administration of a DP-2 antagonist to stimulate hair growth. In some embodiments, the methods comprise (i) genotyping single nucleotide polymorphic loci within or flanking the DP-2 gene in a genomic DNA sample obtained from the subject; and (ii) determining whether the subject is likely to be responsive to administration of the DP-2 antagonist, based on the genotype detected at the loci. In some embodiments, the methods further comprise the step of obtaining genomic DNA from the subject. In some embodiments, the methods comprise the step of amplifying the genomic DNA (e.g., by PCR). In some embodiments, the genomic DNA or amplified genomic DNA is genotyped by sequencing DNA regions that contain the loci. In some embodiments, the genomic DNA or amplified genomic DNA is genotyped by (i) contacting it with detectably labeled oligonucleotides complementary to allele at the loci; and (ii) detecting the presence or absence of (single nucleotide polymorphisms) SNPs at the loci. In some embodiments, the loci comprise one or more, and preferably all, SNPs from rs545659, rs634681, and rs7167.

In another aspect, provided herein are methods of identifying and treating a subject having androgenetic alopecia, baldness or hair loss and who is likely to be responsive to administration of a DP-2 antagonist to stimulate hair growth In some embodiments, the methods comprise (i) identifying as described herein whether the subject is likely to be responsive to administration of a DP-2 antagonist to stimulate hair growth; and (ii) administering a therapeutically effective amount of the DP-2 antagonist to the subject, if the subject has been determined likely to be responsive to the DP-2 antagonist. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are non-therapeutic (i.e., cosmetic) methods of identifying and stimulating hair growth in a subject who is likely to be responsive to administration of a DP-2 antagonist to stimulate hair growth In some embodiments, the methods comprise (i) identifying as described herein whether the subject is likely to be responsive to administration of a DP-2 antagonist to stimulate hair growth; and (ii) administering an effective amount of the DP-2 antagonist to the subject, if the subject has been determined likely to be responsive to the DP-2 antagonist. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are methods of treating a subject having androgenetic alopecia, baldness or hair loss and having one or more alleles indicating that the subject is likely to be responsive to administration of a DP-2 antagonist to stimulate hair growth. In some embodiments, the methods comprise administering to the subject a therapeutically effective amount of the DP-2 antagonist. In some embodiments, the one or more, and preferably all, alleles of SNPs from rs545659, rs634681, and rs7167. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are non-therapeutic (i.e., cosmetic) methods of stimulating hair growth in a subject having one or more alleles indicating that the subject is likely to be responsive to administration of a DP-2 antagonist to stimulate hair growth. In some embodiments, the methods comprise administering to the subject an effective amount of the DP-2 antagonist. In some embodiments, the one or more, and preferably all, alleles of SNPs from rs545659, rs634681, and rs7167. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are DP-2 antagonists and compositions thereof for use in the methods described herein.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
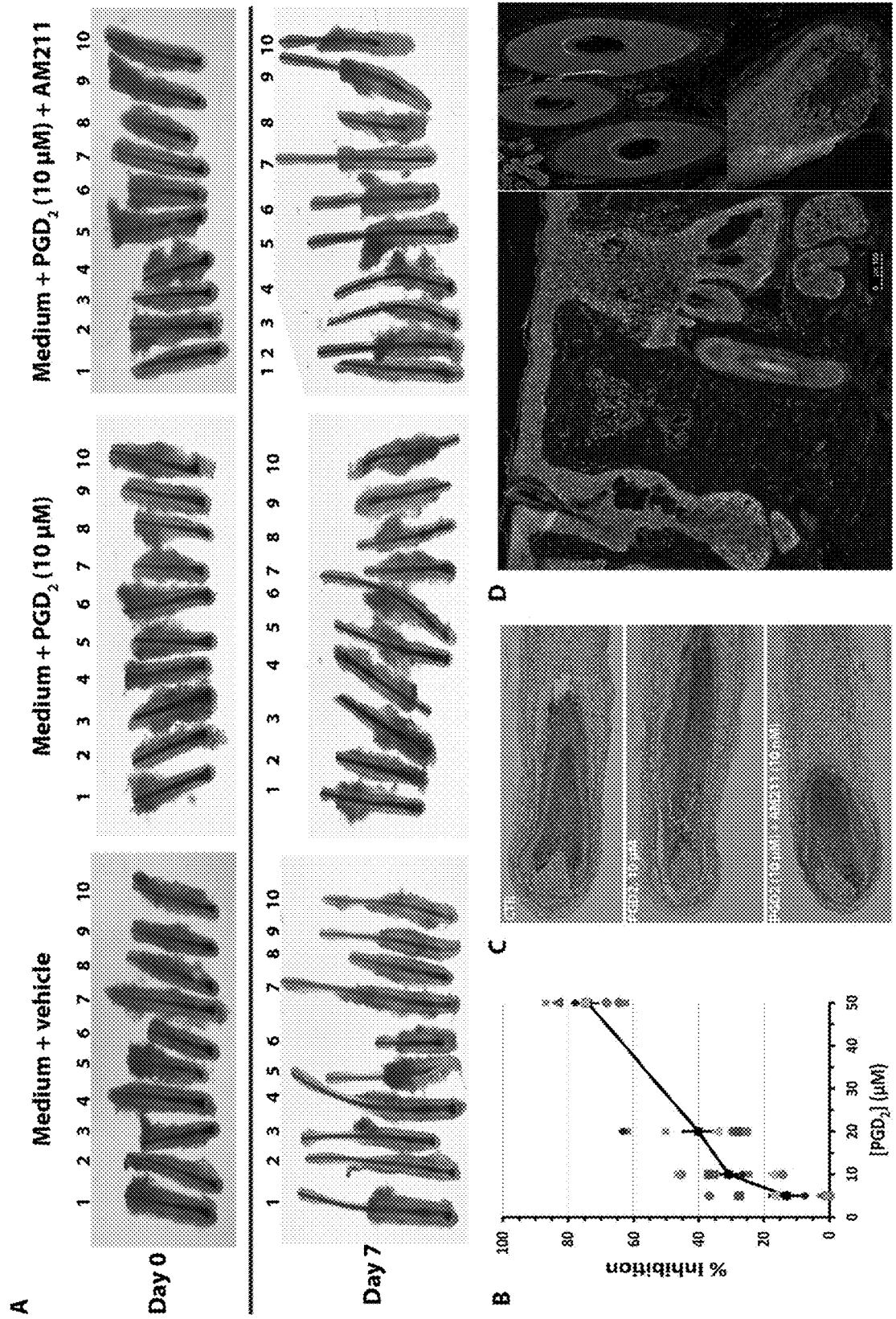
FIG. 1. $PGD_2$ inhibits growth of human hair follicles in explant culture in a dose dependent manner. A. Hair follicles cultured in growth medium for 7 days showed significant growth. The growth was severely inhibited by addition of $PGD_2$ (10 μM) to the culture medium. The presence of a DP-2 antagonist, AM211, at 10 nM rescued hair follicles from the inhibition by $PGD_2$. B. $PGD_2$ exerts its inhibitory effect on hair growth in a dose-dependent manner. C. Representative histological images of hair follicles harvested after 7-day culture. D. In the human scalp, CRTH2/DP-2, the receptor mediating the effects of $PGD_2$ and antagonists, is expressed in the epidermis, hair follicle keratinocytes, and sebaceous gland (SG), but not in dermal papilla (DP). Its expression level is elevated in the bald scalp (left) relative to the normal one (right).

The invention relates to compositions and methods for regulating hair growth. Specifically, the invention relates to identifying subjects, such as those with androgenetic alopecia or baldness or hair loss, susceptible to hair growth inhibition by prostaglandin D2 ($PGD_2$) and responsive to $PGD_2$ receptor, DP-2 (aka CRTH2 or GPR44) antagonists to stimulate hair growth.

Elevated levels of prostaglandin $D_2$ synthase (PTGDS) at the message and protein levels was found in balding versus haired scalp from men with AGA. The enzymatic product of PTGDS, prostaglandin $D_2$ ($PGD_2$), was also found to be elevated in bald human scalp tissue. A close temporal relationship was shown between elevations in both Ptgds mRNA and $PGD_2$ levels in mice with hair follicle regression during normal hair follicle cycling. In addition, functional data also showed that $PGD_2$ and its nonenzymatic metabolite, 15-deoxy-$D_{12,14}$-prostaglandin J2 (15-dPGJ2), inhibit hair growth in both mouse and human hair follicles. In mice and humans, the $PGD_2$-mediated inhibition of hair growth required the G protein (heterotrimeric guanine nucleotide-binding protein)-coupled receptor 44 (GPR44 or DP-2), but not the prostaglandin $D_2$ receptor 1 (Ptgdr or DP-1). Additionally, a mouse model (K14-Ptgs2) with elevated $PGD_2$ levels in the skin phenocopies human AGA. These results demonstrate, among other things, the role of PGD$_2$ and DP-2 in the pathogenesis of AGA for hair treatment.

Surprisingly, hair follicles from a subset of alopecia patients exhibit no growth inhibition by PGD$_2$, indicating the existence of PGD$_2$ responding and non-responding individuals. In addition, SNPs were identified in the CRTH2/DP-2 gene that are associated with sensitivity to PGD$_2$ inhibition of hair growth. The existence of PGD$_2$ responding and non-responding individuals with different genotypes in the DP-2 gene indicates that the former group are more responsive to treatment with a DP-2 antagonist to stimulate hair growth and that sensitivity may vary among DP-2 antagonists.

In another aspect, provided herein are methods of identifying whether a subject having androgenetic alopecia, baldness or hair loss is likely to be responsive to administration of a DP-2 antagonist to stimulate hair growth. In some embodiments, the methods comprise (i) genotyping single nucleotide polymorphic loci within or flanking the DP-2 gene in a genomic DNA sample obtained from the subject; and (ii) determining whether the subject is likely to be responsive to administration of the DP-2 antagonist, based on the genotype detected at the loci. In some embodiments, the methods further comprise the step of obtaining genomic DNA from the subject. In some embodiments, the methods comprise the step of amplifying the genomic DNA (e.g., by PCR). In some embodiments, the genomic DNA or amplified genomic DNA is genotyped by sequencing DNA regions that contain the loci. In some embodiments, the genomic DNA or amplified genomic DNA is genotyped by (i) contacting it with detectably labeled oligonucleotides complementary to allele at the loci; and (ii) detecting the presence or absence of (single nucleotide polymorphisms) SNPs at the loci. In some embodiments, the loci comprise one or more, and preferably all, SNPs from rs545659, rs634681, and rs7167.

In another aspect, provided herein are methods of identifying and treating a subject having androgenetic alopecia, baldness or hair loss and who is likely to be responsive to administration of a DP-2 antagonist to stimulate hair growth In some embodiments, the methods comprise (i) identifying as described herein whether the subject is likely to be responsive to administration of a DP-2 antagonist to stimulate hair growth; and (ii) administering a therapeutically effective amount of the DP-2 antagonist to the subject, if the subject has been determined likely to be responsive to the DP-2 antagonist. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are non-therapeutic (i.e., cosmetic) methods of identifying and stimulating hair growth in a subject who is likely to be responsive to administration of a DP-2 antagonist to stimulate hair growth In some embodiments, the methods comprise (i) identifying as described herein whether the subject is likely to be responsive to administration of a DP-2 antagonist to stimulate hair growth; and (ii) administering an effective amount of the DP-2 antagonist to the subject, if the subject has been determined likely to be responsive to the DP-2 antagonist. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are methods of treating a subject having androgenetic alopecia, baldness or hair loss and having one or more alleles indicating that the subject is likely to be responsive to administration of a DP-2 antagonist to stimulate hair growth. In some embodiments, the methods comprise administering to the subject a therapeutically effective amount of the DP-2 antagonist. In some embodiments, the one or more, and preferably all, alleles of SNPs from rs545659, rs634681, and rs7167. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are non-therapeutic (i.e., cosmetic) methods of stimulating hair growth in a subject having one or more alleles indicating that the subject is likely to be responsive to administration of a DP-2 antagonist to stimulate hair growth. In some embodiments, the methods comprise administering to the subject an effective amount of the DP-2 antagonist. In some embodiments, the one or more, and preferably all, alleles of SNPs from rs545659, rs634681, and rs7167. In some embodiments, the DP-2 antagonist is administered topically. In some embodiments, the DP-2 antagonist is administered orally. In some embodiments, the methods further include administering finasteride or minoxidil to the subject. In some embodiments, the methods further include transplanting hair follicles to the subject. In some embodiments, the methods further include removing dermis or epidermis from skin in the subject.

In another aspect, provided herein are DP-2 antagonists and compositions thereof for use in the methods described herein.

As used herein, a "DP-2 antagonist" is a molecule that is able to decrease the amount or activity of DP-2, either within a cell or within a physiological system. For example, a DP-2 antagonist is a substance that can bind selectively to DP-2 receptor and inhibit the physiological action of the DP-2 receptor.

DP-2 antagonists are known in the art. Examples of some DP-2 antagonists are shown in Table 1:

TABLE 1

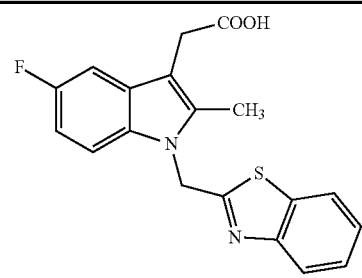

6

TABLE 1-continued
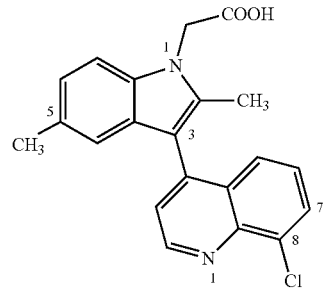 [SMILES: Cc1ccc2c(c1)c(-c1ccnc3c(Cl)cccc13)c(C)n2CC(=O)O]
7
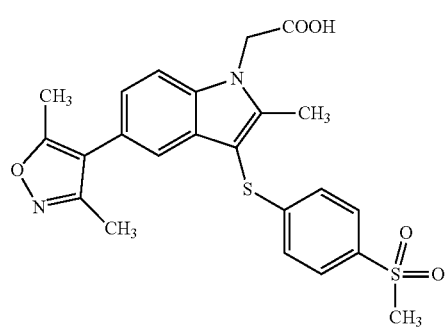 [SMILES: Cc1noc(C)c1-c1ccc2c(c1)c(Sc1ccc(S(C)(=O)=O)cc1)c(C)n2CC(=O)O]
8
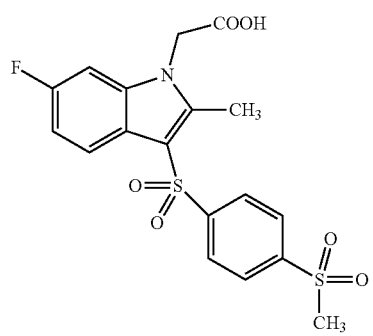 [SMILES: Cc1c(S(=O)(=O)c2ccc(S(C)(=O)=O)cc2)c2ccc(F)cc2n1CC(=O)O]
9
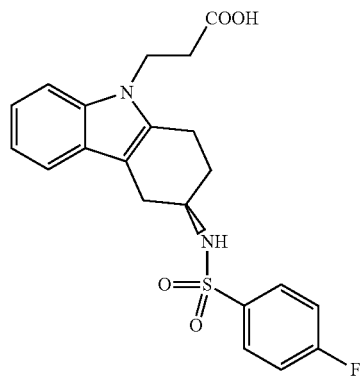
Ramatroban
TABLE 1-continued
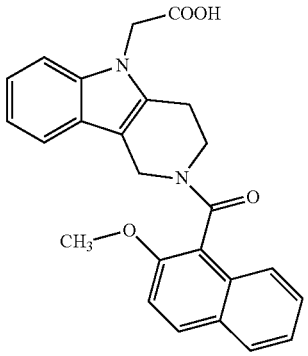 [SMILES: COc1ccc2ccccc2c1C(=O)N1CCc2c(c3ccccc3n2CC(=O)O)C1]
10
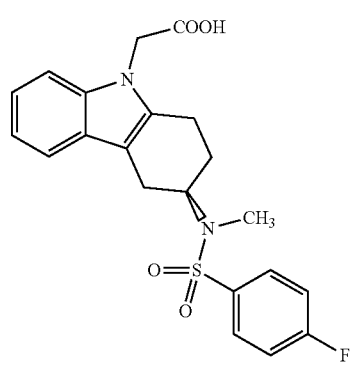 [SMILES: CN([C@@H]1CCc2c(c3ccccc3n2CC(=O)O)C1)S(=O)(=O)c1ccc(F)cc1]
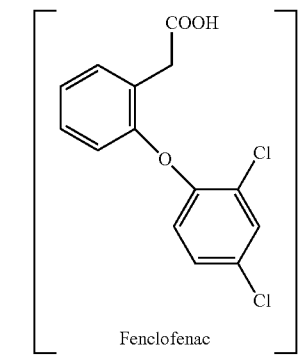
Fenclofenac
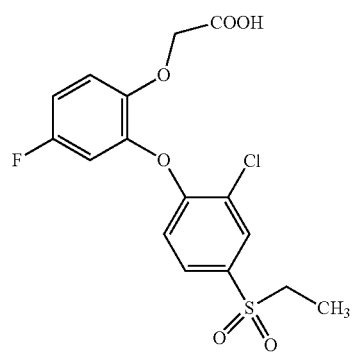 [SMILES: CCS(=O)(=O)c1ccc(Oc2cc(F)ccc2OCC(=O)O)c(Cl)c1]
11

TABLE 1-continued

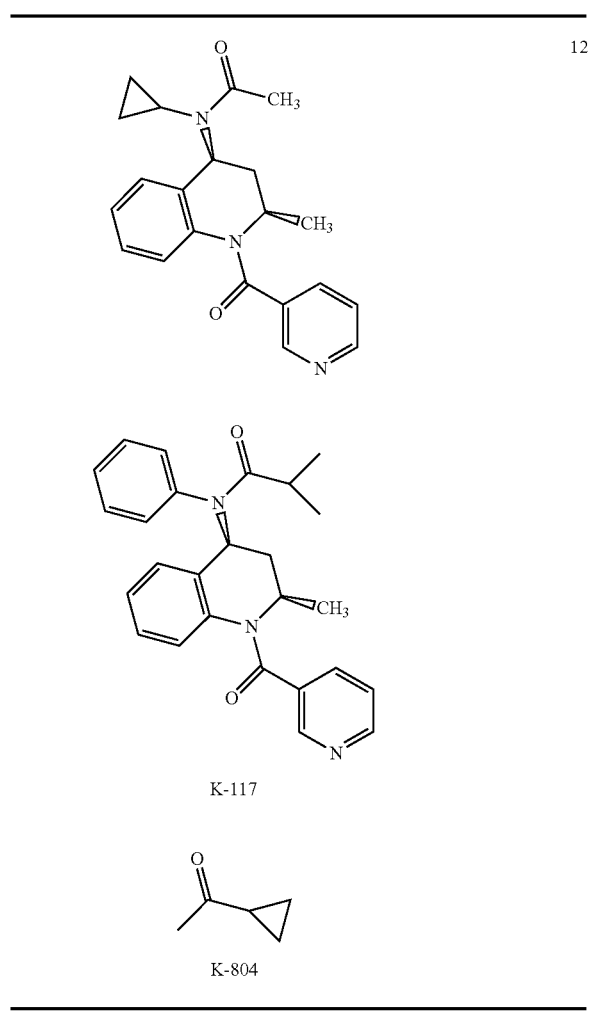

DP-2 antagonists can be divided into a number of classes. One class is Ramatroban and its analogs, examples of which are shown in Tables 1 and 2 (TM30642-3-{3-[(4-fluoro-benzenesulfonyl)-methyl-amino]-1,2,3,4-tetrahydro-carbazol-9-yl}-propionic acid; TM30643-[3-(4-fluoro-benzenesulfo-nylamino)-1,2,3,4-tetrahydro-carbazol-9-yl]-acetic acid; TM30089-{3-[(4-fluoro-benzenesulfonyl)-methyl-amino]-1,2,3,4-tetrahydro-carbazol-9-yl}-acetic acid.

TABLE 2

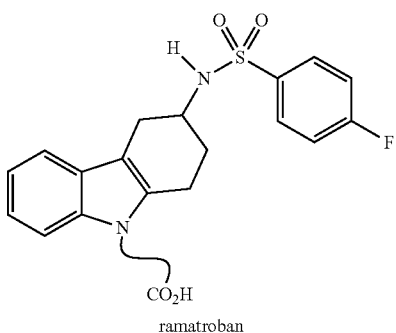

ramatroban

TABLE 2-continued

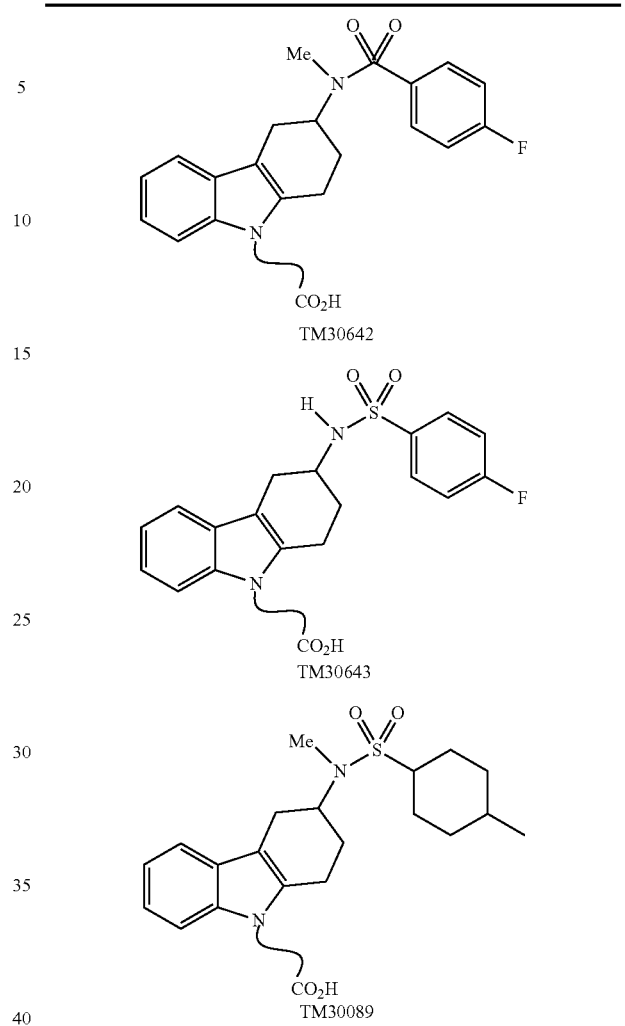

Another class of DP-2 antagonists are indole acetic acid derivatives. Examples of this class of compounds are compounds 6-9 of Table 1.

Another class of DP-2 antagonists are phenyl acetic acid derivatives. An example of this class of compounds, based on fenclofenac is compound 11 of Table 1.

Yet another class of DP-2 antagonists are tetrahydroquinoline derivatives. Examples of this class of compounds are compounds 12, K117 and K-104 of Table 1.

Certain preferred DP-2 antagonists for use in the methods and compositions provided herein are DP-2 antagonists that have been the subject of at least one clinical trial. Examples of DP-2 antagonists that have been the subject of at least one clinical trial include, but are not limited to, those listed in Table 3 below:

TABLE 3

Clinical Stage DP-2 Antagonists

| Company | Compound ID | Status | Reference[a] |
|---|---|---|---|
| Actelion | ACT-129968 (Setipiprant) | Phase IIb | NCT01225315 |
| Actimis | AP768 | Phase I | |
| Amira | AM211 | Phase I | |

TABLE 3-continued

Clinical Stage DP-2 Antagonists

| Company | Compound ID | Status | Reference[a] |
|---|---|---|---|
| Amira | AM461 | Phase I | |
| Amgen | AMG853 | Discontinued after Phase II (2011) | NCT01018550 |
| Array BioPharma | ARRY-502 | Phase I | NCT01349725 |
| AstraZeneca | AZD1981 | Phase II | NCT01197794 |
| AstraZeneca | AZD8075 | Discontinued after Phase I (2010) | NCT00787072 |
| AstraZeneca | AZD5985 | Discontinued after Phase I (2010) | NCT00967356 |
| Merck | MK-7246) | Phase I | |
| Novartis | QAV680 | Phase II completed | NCT00814216 |
| Oxagen | OC000459 | Phase IIb | NCT01057927 |
| Oxagen | OC002417 | Back-up candidate | |
| Pulmagen | ADC3680B | Phase I | NCT01173770 |
| Shionogi | S-555739 | Phase IIb (Japan) | |

[a]NCT numbers can be searched at the website: www.clinicaltrials.gov

One DP-2 antagonist contemplated for use in the methods and compositions provided herein is the DP-2 antagonist setipiprant. Its structure is provided below:

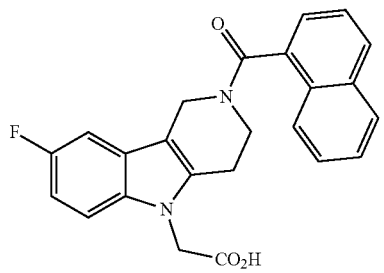 [SMILES: O=C(O)Cn1c2c(c3cc(F)ccc31)CN(C(=O)c1cccc3ccccc13)CC2]

One DP-2 antagonist contemplated for use in the methods and compositions provided herein is the DP-2 antagonist fevipiprant (QAW 039). Its structure is provided below:

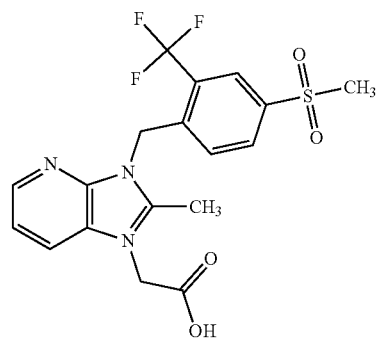

One DP-2 antagonist contemplated for use in the methods and compositions provided herein is the DP-2 antagonist AM211 whose structure is provided below:

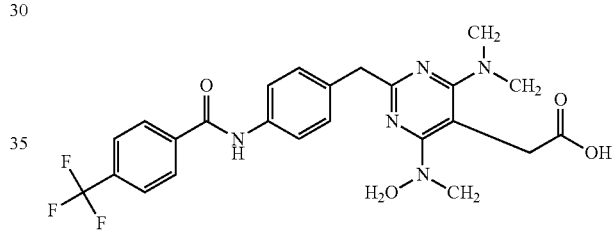

CRTH2 $IC_{50}$ = 4.9 nM
WB $IC_{50}$ = 2.7 nM

One DP-2 antagonist contemplated for use in the methods and compositions provided herein is the DP-2 antagonist BI 671800. Its structure is provided below:

One DP-2 antagonist contemplated for use in the methods and compositions provided herein is the DP-2 antagonist Ramatroban. Its structure is provided below:

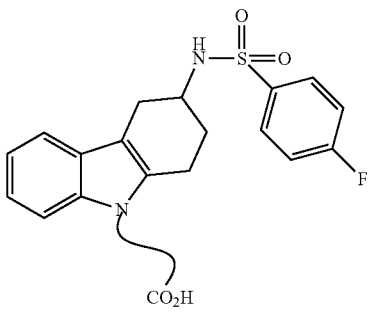

CRTH2 $K_i$ = 70 nM

One DP-2 antagonist contemplated for use in the methods and compositions provided herein is the DP-2 antagonist whose structure is provided below:

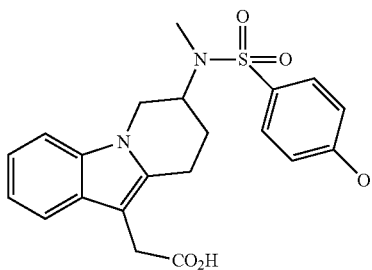

CRTH2 IC$_{50}$ = 2.7 nM
WB IC$_{50}$ = 2.2 nM

One DP-2 antagonist contemplated for use in the methods and compositions provided herein is the DP-2 antagonist AZD1981. Its structure is provided below:

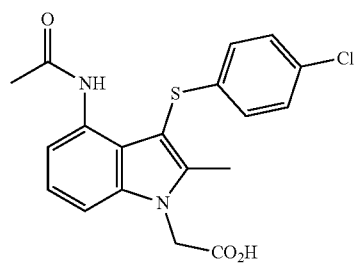

CRTH2 IC$_{50}$ = 4.3 nM

One DP-2 antagonist contemplated for use in the methods and compositions provided herein is the DP-2 antagonist whose structure is provided below:

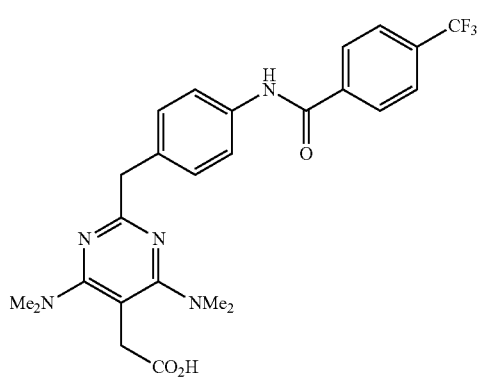

CRTH2 Ki = NT
WB IC$_{50}$ = 626 nM*

One DP-2 antagonist contemplated for use in the methods and compositions provided herein is the DP-2 antagonist whose structure is provided below:

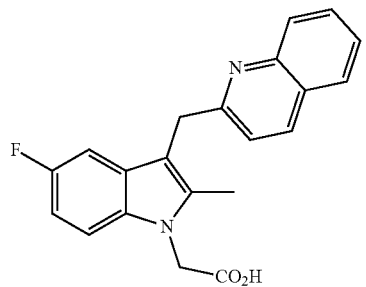

CRTH2 Ki = 13 nM
WB IC$_{50}$ = 100 nM
WB pK$_6$ = 7.5

One DP-2 antagonist contemplated for use in the methods and compositions provided herein is the DP-2 antagonist AMG853. Its structure is provided below:

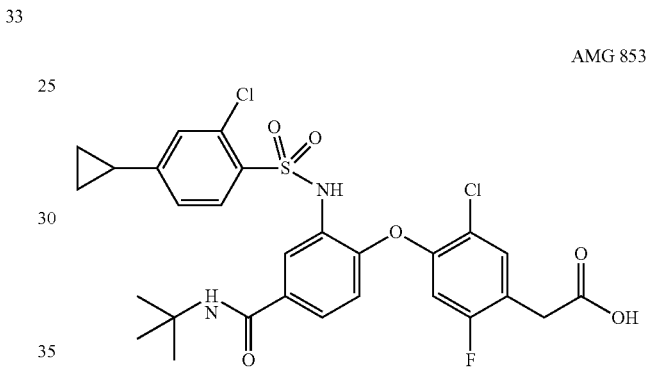

AMG 853

Additional DP-2 antagonists can be found in the following publications: EP1,170,594, EP1,435,356 WO2003/066046, WO2003/066047, WO2003/097042, WO2003/101961, WO2003/101981, WO2004/007451, WO2004/032848, WO2004/035543, WO2004/106302, WO2005/019171, WO2005/054232, WO2005/018529, WO2005/040112, GB2,407,318, WO2005/040114, WO2005/044260, WO2005/095397, WO2005/100321, WO2005/102338, 10 WO2006/095183, WO2007/107772, U.S. Pat. No. 7,405, 215, each of which is hereby incorporated by reference in its entirety.

The compositions described herein may include an "effective amount." An "effective amount" refers to an amount effective, at dosages and for periods of time necessary, to achieve the desired result. An effective amount of a molecule may vary according to factors such as the state, age, sex, and weight of the individual, and the ability of the molecule to elicit a desired response in the individual. An effective amount is also one in which any toxic or detrimental effects of the molecule are outweighed by the beneficial effects.

Provided herein are compositions comprising a DP-2 antagonist. For example, provided herein are compositions for stimulating hair growth in a subject, the compositions comprising: a DP-2 antagonist in an amount effective to enhance hair growth in the subject. In another example, provided herein are compositions for treating androgenetic alopecia or baldness or hair loss in a subject, the compositions comprising: a DP-2 antagonist in an amount effective to treat said androgenetic alopecia or baldness or hair loss in said subject. In another example, provided herein are pharmaceutical compositions comprising a DP-2 antagonist and at least one pharmaceutically acceptable excipient or carrier.

"Pharmaceutically acceptable carriers" include any excipient which is nontoxic to the cell or subject being exposed thereto at the dosages and concentrations employed. Pharmaceutical compositions may also include one or more additional therapeutic agents. Pharmaceutically acceptable carriers include solvents, dispersion media, buffers, coatings, antibacterial and antifungal agents, wetting agents, preservatives, buggers, chelating agents, antioxidants, isotonic agents and absorption delaying agents. Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

The pharmaceutical compositions provided herein may be formulated in a variety of ways, including for example, solid, semi-solid (e.g., cream, ointment, and gel), and liquid dosage forms, such as liquid solutions (e.g., topical lotion or spray), dispersions or suspensions, tablets, pills, powders, liposomes and suppositories. In some embodiments, the compositions are in the form of injectable or infusible solutions. The compositions may be in a form suitable for oral, intravenous, intraarterial, intramuscular, subcutaneous, parenteral, transmucosal, transdermal, or topical administration. Preferably, the compositions are formulated for oral or topical administration. The composition may be formulated as an immediate, controlled, extended or delayed release composition.

More particularly, pharmaceutical compositions suitable for use include sterile aqueous solutions (where water soluble) or dispersions and sterile powders for the extemporaneous preparation of sterile solutions or dispersions. They should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

The compositions may also include isotonic agents, for example, sugars, polyalcohols, such as mannitol, sorbitol, or sodium chloride. Prolonged absorption of injectable compositions can be brought about by including in the composition an agent which delays absorption, for example, aluminum monostearate and gelatin.

Sterile solutions can be prepared by incorporating the molecule, by itself or in combination with other active agents, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in US2002/0102208, which is incorporated herein by reference in its entirety. Such articles of manufacture will preferably have labels or package inserts indicating that the associated compositions are useful for treating a subject suffering from, or predisposed to androgenetic alopecia, baldness or hair loss.

Effective doses of the compositions described herein, for the methods described herein vary depending upon many different factors, including the specific antagonist used, the sensitivity of the subject for that antagonist, means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which toxic or detrimental effects of the molecule are outweighed by the therapeutically beneficial effects.

Further provided herein are kits comprising a therapeutically effective amount of a DP-2 antagonist. Also provided herein are methods of treating a disease or condition, comprising administering to a subject in need thereof a therapeutically effective amount of a DP-2 antagonist.

As used herein, the term, "selective" with respect to inhibition or stimulation means preferential inhibition or stimulation, respectively, of a first activity relative to a second activity (e.g., preferential inhibition of one pathway to another pathway; preferential inhibition relative to other receptors; or preferential inhibition of a mutant to a wild-type or vice versa). In some embodiments, the inhibitor is greater than five times more selective, greater than ten times more selective, greater than fifty times more selective, greater than 100 times more selective, or greater than 1000 times more selective for the desired molecular target or pathway versus an undesired molecular target or pathway. In some embodiments, an antagonist or agonist will inhibit or stimulate, respectively, the first activity of the molecular target or pathway by at least 2-fold, at least 5-fold, at least 10-fold, at least 20-fold, at least 50-fold, at least 100-fold relative to the second activity under the same conditions. It will be appreciated that in preferred embodiments, the DP-2 antagonist, will be selective with respect to DP-1 by any of the foregoing amounts. The activity of a molecular target or pathway may be measured by any reproducible means and may be measured in vitro or in vivo.

As used herein, "modulating" refers to "stimulating" or "inhibiting" an activity of a molecular target or pathway. For example, a composition modulates the activity of a molecular target or pathway if it stimulates or inhibits the activity of the molecular target or pathway by at least 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more relative to the activity of the molecular target or pathway under the same conditions but lacking only the presence of the composition. In another example, a composition modulates the activity of a molecular target or pathway if it stimulates or inhibits the activity of the molecular target or pathway by at least 2-fold, at least 5-fold, at least 10-fold, at least 20-fold, at least 50-fold, at least 100-fold relative to the activity of the molecular target or pathway under the same conditions but lacking only the presence of the composition. The activity of a molecular target or pathway may be measured by any reproducible means. The activity of a molecular target or pathway may be measured in vitro or in vivo by an appropriate assay known in the art. Control samples (untreated with the composition) can be assigned a relative activity value of 100%. A change in activity caused by the composition can be measured in the assays.

It will be appreciated that many of the antagonists described herein are strong inhibitors of their targets. For example, an antagonist may have a binding inhibitory activity ($IC_{50}$ value) for its desired molecular target (i.e., DP-2) of 1000 µM or less, 1000 nM or less, 100 nM or less, 10 nM or less, or especially 1 nM or less. In another example, the inhibitor has a binding inhibitory activity ($IC_{50}$ value) for its desired molecular target of between 1000 µM and 1 nM, between 1000 µM and 10 nM, between 1000 µM and 100 nM, between 1000 µM and 1000 nM, between 1000 nM and 1 nM, between 1000 nM and 10 nM, between 1000 nM and 100 nM, between 100 nM and 10 nM, between 100 nM and 1 nM, or between 10 nM and 1 nM.

In some embodiments, the antagonists disclosed herein inhibit their molecular targets or pathways by at least about 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more.

Various dosage ranges are contemplated and may vary based on the antagonist used and the sensitivity of the subject for that antagonist. For example, the dose of the antagonist is between about 0.1-1000 mg/day, about 1-1000 mg/day about 5-500 mg/day, about 10-300 mg/day, about 20-200 mg/day, about 40-150 mg/day, about 60-100 mg/day, about 0.1-100 mg/day, about 0.1-50 mg/day, about 0.1-20 mg/day, about 0.1-10 mg/day, about 0.1-5 mg/day, or about 0.5-5 mg/day.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

As used herein, a "polymorphic locus" is a genomic locus at which two or more alleles have been identified. As used herein, an "allele" is one of two or more existing genetic variants of a specific polymorphic genomic locus. As used herein, a "single nucleotide polymorphism" or "SNP" is a particular base position in the genome where alternative bases are known.

As used herein, "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a", three genotypes can be formed: A/A, A/a, and a/a. As used herein, "genotyping" refers to an experimental, computational, or observational protocol for distinguishing an individual's genotype at one or more well-defined loci.

In one embodiment, treating hair loss refers to treating a disease or disorder comprising balding. In another embodiment, treating hair loss refers to treating androgenetic alopecia (AGA). In another embodiment, treating hair loss refers to treating a disease or disorder which is male pattern baldness. In another embodiment, treating hair loss refers to treating a disease or disorder which is female pattern baldness. In one embodiment, treating hair loss refers to treating or preventing any type of hair loss in any area of the body, including, but are not limited to, scalp and eyebrow.

In another embodiment, treating hair loss refers to treating a disease or disorder associated with hair loss. In another embodiment, treating hair loss refers to treating a hair loss disease or disorder associated with a discoid lupus erythematosis. In another embodiment, treating hair loss refers to treating a hair loss disease or disorder associated with a congenital hypotrichosis. In another embodiment, treating hair loss refers to treating a hair loss disease or disorder associated with a lichen planopilaris. In another embodiment, treating hair loss refers to treating a scarring alopecia.

The DP-2 antagonist may be administered alone, or in combination with one or more other therapeutically effective agents (e.g., finasteride, minoxidil, or both) or treatments. The other therapeutically effective agent may be conjugated to the DP-2 antagonist, incorporated into the same composition as the DP-2 antagonist, or may be administered as a separate composition. The other therapeutically agent or treatment may be administered prior to, during and/or after the administration of the DP-2 antagonist. In another embodiment, DP-2 antagonist is administered independently from the administration of a hair promoting agent. In one embodiment, DP-2 antagonist is administered first, followed by the administration of a hair promoting agent. In another embodiment, a hair promoting agent is administered first, followed by the administration of DP-2 antagonist.

Other therapeutically effective agents/treatments for a combination therapy to enhance hair growth include, for example, but not limited to, transplantation surgery and removing dermis or epidermis.

The administration of the DP-2 antagonist with other agents and/or treatments may occur simultaneously, or separately, via the same or different route, at the same or different times. Dosage regimens may be adjusted to provide the optimum desired response (e.g., a therapeutic or prophylactic response).

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The compositions described herein may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, topical, transdermal, oral (for example, in capsules, suspensions or tablets), parenteral (including subcutaneous, intravenous, intramedullary, intraarticular, intramuscular, or intraperitoneal injection), or rectal. Administration to a subject may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is a male human or a female human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

Compounds described herein can also be prepared as prodrugs, for example pharmaceutically acceptable prodrugs. The terms "pro-drug" and "prodrug" are used interchangeably herein and may refer to any compound which releases an active parent drug in vivo. Since prodrugs are known to enhance numerous desirable qualities of pharmaceuticals (e.g., solubility, bioavailability, manufacturing, etc.) the compounds described herein can be delivered in prodrug form.

The term "about" or "approximately" means within an acceptable error range for the particular value as determined by one of ordinary skill in the art, which will depend in part on how the value is measured or determined.

In some embodiments, the methods comprise obtaining a genomic DNA sample from a subject. For example, a biologic sample from an individual can first be obtained. Such biological samples include, but are not limited to, a bodily fluid (such as urine, saliva, plasma, or serum) or a tissue sample (such as a buccal tissue sample or buccal cell). The biologic sample can then be used to obtain or amplify genomic DNA using known methods.

Nucleic acid mutations can be determined by any of a number of known procedures. In some embodiments, DNA arrays can be used to analyze at least a portion of the genomic sequence of the individual. Exemplary DNA arrays include GeneChip Arrays, GenFlex Tag arrays, and Genome-Wide Human SNP Array 6.0 (available from Affymetrix, Santa Clara, CA).

In certain embodiments, whole or partial genome sequence information is. Such sequences can be determined using standard sequencing methods including chain-termination (Sanger dideoxynucleotide), dye-terminator sequencing, and SOLiD™ sequencing (Applied Biosystems). Genome sequences can be cut by restriction enzymes or sheared (mechanically) into shorter fragments for sequencing. DNA sequences can also be amplified using known methods such as PCR and vector-based cloning methods (e.g., *Escherichia coli*).

In some embodiments, at least a portion of an individual's genetic material (e.g., DNA, RNA, mRNA, cDNA, other nucleotide bases or derivative thereof) is scanned or sequenced using, e.g., conventional DNA sequencers or chip-based technologies, to identify the presence or absence of one or more SNPs and their corresponding alleles.

Any patent, patent application publication, or scientific publication, cited herein, is incorporated by reference herein in its entirety.

The following examples are presented in order to more fully illustrate the preferred embodiments of the invention. They should in no way be construed, however, as limiting the broad scope of the invention.

EXAMPLES

CRTH2/DP-2 Antagonists Reverse Hair Growth Inhibition Caused by $PGD_2$

Androgenetic alopecia (AGA) is the most common type of hair loss, affecting approximately 50% of men and 30% of women by the age of 50. In addition to testosterone, which is a necessary factor for the development of AGA in men, other contributing factors remain unknown. Blocking the conversion of testosterone to its more potent form, dihydrotestosterone, through administration of the pharmacological agent finasteride (Propecia) benefits patients with early AGA but fails to reverse hair miniaturization completely. This suggests that the development of more effective treatment depends on identifying additional factors that also contribute to the development of AGA.

Toward this goal we previously used a global gene expression approach to find differentially expressed genes in balding versus non-balding scalp from the same individuals (Garza et al. (2012) Sci. Transl. Med. 4, 126ra34). We found elevated levels of prostaglandin $D_2$ synthase (PTGDS) and its catalytic product, $PGD_2$, in balding scalp from men. We further provided functional data indicating that $PGD_2$ inhibits hair growth and the inhibition was mediated through the DP-2 receptor (aka GPR44, CRTH2) in the Gpr44 knockout mouse. That elevated levels of $PGD_2$ causes hair loss was further validated in a mouse model (K14-Ptgs2) engineered to produce increased $PGD_2$ levels in the skin. These mice suffer progressive miniaturization of hair follicles and hyperplasia of sebaceous glands, both hallmarks of human AGA. These results implicate $PGD_2$ as playing a causative role in AGA and provide novel targets for pharmacological interventions aimed at preventing hair loss and promoting hair growth.

In this Example, multiple DP-2 antagonists were tested on human hair follicle growth in an organ culture system, and the effect of DP-2 antagonists on the hair cycle in vivo in mice was studied.

Materials and Methods

Tissue: Scalp was obtained from normally discarded human skin samples from CHTN and from men and women undergoing hair transplantation (IRB exempted study Protocol #818053).

DP-2 antagonists used: AM211 (Amira), Setipirant (Actelion; data not shown).

Hair follicle organ culture: Hair follicles were microdissected from discarded tissues from hair transplant patients and cultured for seven days as described by Philpott et al. (J. Dermatol. Sci. Suppl: S55-72. (1994)) in the presence or absence of $PGD_2$ and/or DP-2 antagonist, with a change of culture medium every two days. Hair follicles were photographed at the beginning and end of the culture period. Hair follicle growth was measured from the photographs using Image J software.

Immunostaining: Immunofluorescence analysis with anti-Ki67 and anti-Caspase-3 was performed on cryosections of cultured hair follicles or whole mount hair follicles fixed in 4% PFA. Images were photographed with Leica fluorescence microscope.

Animal studies: The back skins of C57BL mice at 6-7 week were depilated. DP-2 antagonists were dissolved in 95% EtOH/2% Glycerol/3% PEG. 100 µL of each compound was spread on the shaved back skin once daily for 2 weeks starting from day 8 post depilation. At day 22 post depilation hair shafts were plucked for hair length measurement and skins were harvested for histological assessment of hair cycle stages.

SNP analysis: Genomic DNA was extracted from 35 donors (Group 1) including 21 that are sensitive and 14 that are not sensitive to $PGD_2$ inhibition in hair follicle organ culture. Subsequently, 88 new samples were collected, and of these, 65 donors (Group 2) had usable culture data. The entire human DP-2 gene (containing two exons and one intron) as well as 4 kb flanking regions were amplified by multiplex PCR and sequenced by Iron Torrent Sequencing method. The SNP association to $PGD_2$ sensitivity was analyzed by Fisher's Exact Test.

Results and Discussion $PGD_2$ inhibits growth of human hair follicles in explant culture in a dose dependent manner (FIG. 1). Hair follicles cultured in growth medium for 7 days showed significant growth. But the growth was severely inhibited by addition of $PGD_2$ (10 µM) to the culture medium, while the presence of a DP-2 antagonist, AM211, at 10 nM rescued hair follicles from the inhibition by $PGD_2$ (FIG. 1A). B. $PGD_2$ exerts its inhibitory effect on hair growth in a dose-dependent manner (FIG. 1B). Representative histological images of hair follicles harvested after 7-day culture are shown in FIG. 1C. D. In the human scalp, CRTH2/DP-2, the receptor mediating the effects of $PGD_2$ and antagonists, is expressed in the epidermis, hair follicle keratinocytes, and sebaceous gland (SG), but not in dermal papilla (DP) (FIG. 1D). Its expression level is elevated in the bald scalp (FIG. 1D, left) relative to the normal one (FIG. 1D, right).

Figure 2:
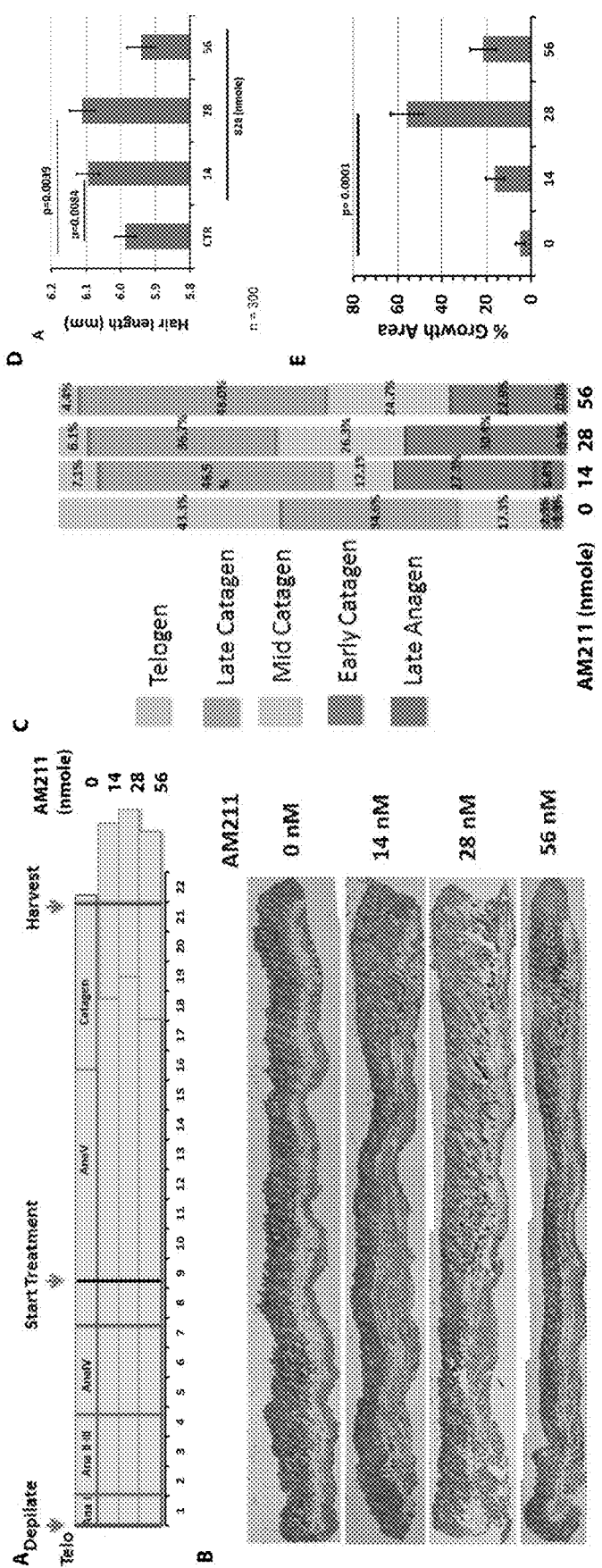
FIG. 2. Antagonists of CRTH2/DP-2 extend anagen, the growing phase of the mouse hair cycle, and increase the length of the hair shaft. A. To test the effects on DP-2 antagonists on hair growth in vivo, AM211 was applied topically at the indicated doses, once per day for two weeks, to the back skin of 6-7 week old mice 8 days after hair depilation. The hair shafts and skins of the treated mice were harvested at day 22 post depilation for length measurement and hair cycle stage analysis, respectively. B. Representative images of the histological sections of skin from treated mice. Based on morphological assessment, hair follicles in the sections were classified into one of the hair cycle stages and counted. C. In the control group (treated with vehicle only), nearly all hair follicles had entered the catagen and telogen phase, while AM211-treated groups showed a dose-dependent delay in hair follicles entering catagen. D & E. As a result of an extended anagen, skins of AM211-treated mice had a larger area with hair follicles continuing to grow and produced longer hair shaft.

To test the effects on DP-2 antagonists on hair growth in vivo, AM211 was applied topically at the indicated doses, once per day for two weeks, to the back skin of 6-7 week old mice 8 days after hair depilation (FIG. 2A). The hair shafts and skins of the treated mice were harvested at day 22 post depilation for length measurement and hair cycle stage analysis, respectively. Representative images of the histological sections of skin from treated mice are shown in FIG. 2B. Based on morphological assessment, hair follicles in the sections were classified into one of the hair cycle stages and counted. In the control group (treated with vehicle only), nearly all hair follicles had entered the catagen and telogen phase, while AM211-treated groups showed a dose-dependent delay in hair follicles entering catagen (FIG. 2C). As a result of an extended anagen, skins of AM211-treated mice had a larger area with hair follicles continuing to grow and produced longer hair shaft (FIGS. 2D & 2E).

Figure 3:
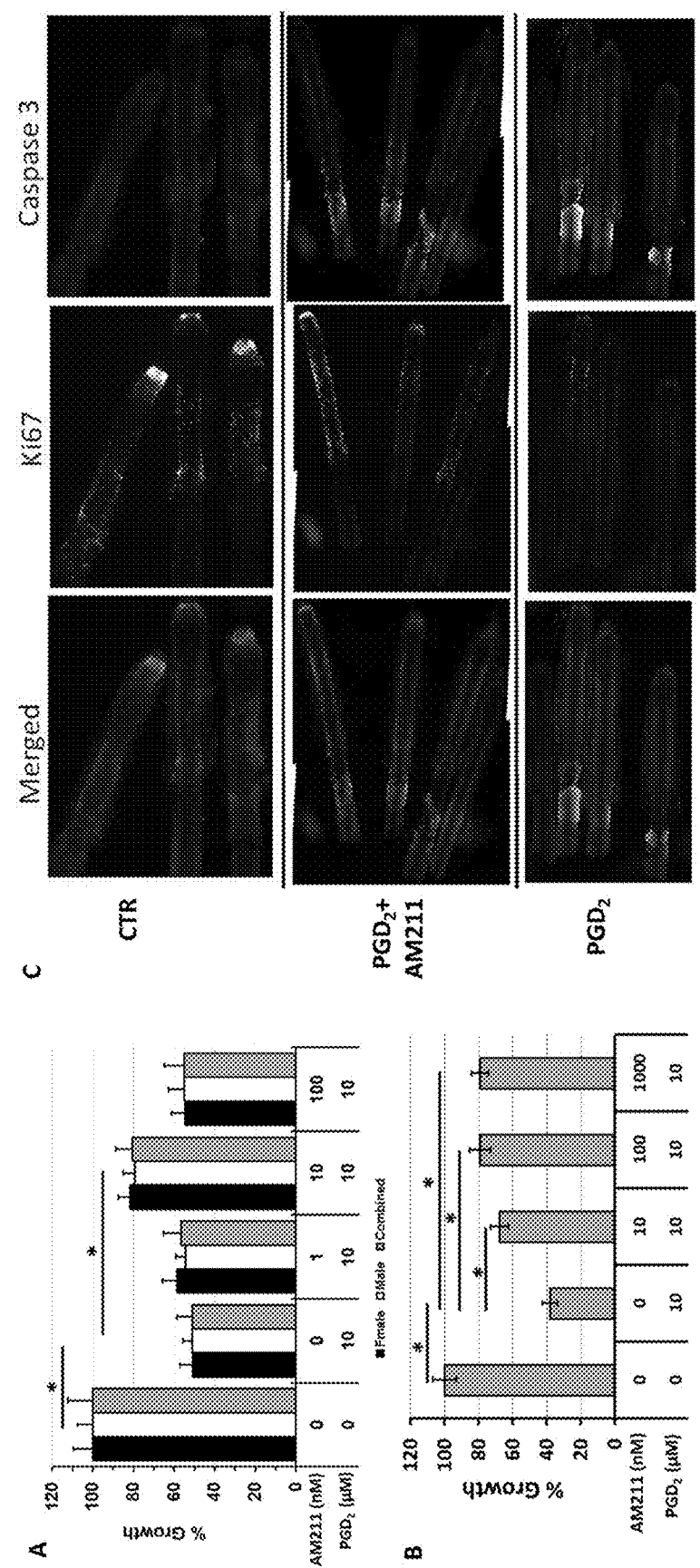
FIG. 3. Antagonists of CRTH2/DP-2 reverse hair follicle growth inhibition by $PGD_2$. A. In explant culture, human male and female hair follicles responded similarly to the inhibitory activity of $PGD_2$ as well as to the anti-$PGD_2$ activity of DP-2 antagonists. The reduction in anti-$PGD_2$ effect seen at high doses of AM211 was likely due to an unidentified contaminant in AM211 preparation, which was purified to 95% homogeneity, since the use of a 99.5% pure preparation of AM211 at high doses led to sustained anti-$PGD_2$ activity (see B). *p<0.001. C. Immunofluorescence staining of cultured hair follicles for markers of proliferation (Ki67, shown in red) and apoptosis (active caspase 3, shown in green) revealed that $PGD_2$ suppressed proliferation and promoted apoptosis of hair follicle keratinocytes. DP-2 antagonist reversed these two $PGD_2$-triggered cellular events in hair follicles.

In explant culture, human male and female hair follicles responded similarly to the inhibitory activity of $PGD_2$ as well as to the anti-$PGD_2$ activity of DP-2 antagonists (FIG. 3A). The reduction in anti-$PGD_2$ effect seen at high doses of AM211 was likely due to an unidentified contaminant in AM211 preparation, which was purified to 95% homogeneity, since the use of a 99.5% pure preparation of AM211 at high doses led to sustained anti-$PGD_2$ activity (see FIG. 3B). Immunofluorescence staining of cultured hair follicles for markers of proliferation (Ki67, shown in red) and apoptosis (active caspase 3, shown in green) revealed that $PGD_2$ suppressed proliferation and promoted apoptosis of hair follicle keratinocytes (FIG. 3C). DP-2 antagonist reversed these two $PGD_2$-triggered cellular events in hair follicles.

Figure 4:
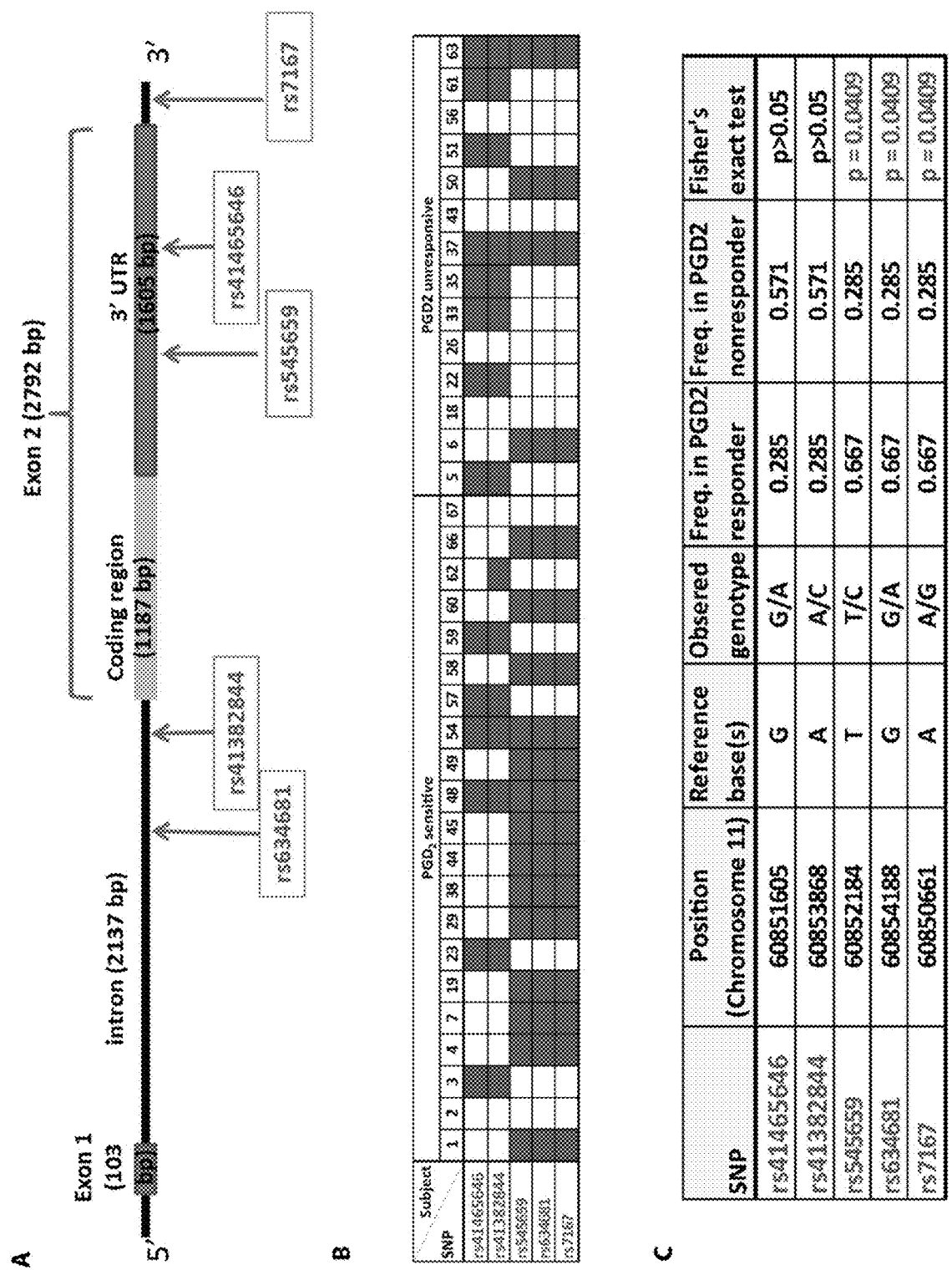
FIG. 4. Identification of SNPs in the human CRTH2/DP-2 gene that correlate with inhibition of hair growth by $PGD_2$ in explant culture. A. The locations of human CRTH2/DP-2 SNPs, initially identified as potential candidates for markers of susceptibility to $PGD_2$ activity. Human CRTH2/DP-2 gene is located on chromosome 11. B. Of the 35 patients tested, hair follicles from 21 patients exhibited $PGD_2$-mediated growth inhibition while those from the remaining 14 were not affected in their growth by $PGD_2$. DNA sequencing of CRTH2/DP-2 gene as well as SNP PCR showed that roughly 70% of the $PGD_2$-sentitive individuals carry all three SNPs: rs545659, rs634681, and rs7167 (shown in red). C. Fisher exact test showed that these three SNPs very likely linked to the sensitivity of these patients to $PGD_2$ inhibition.

SNPs were identified in the human CRTH2/DP-2 gene, which is located on chromosome 11, that correlate with inhibition of hair growth by $PGD_2$ in explant culture (FIG. 4). FIGS. 4A and C shows the locations of five (out of 61) human CRTH2/DP-2 SNPs, initially identified as potential candidates for markers of susceptibility to $PGD_2$ activity. Those five potential candidates were: (1) rs545659 with T as the reference base and with C as a minor allele having a minor allele frequency (MAF) of 0.338; (2) rs634681 with G as the reference base and with A as a minor allele having a MAF of 0.335; (3) rs7167 with A as the reference base and with G as a minor allele having a MAF of 0.338; (4) rs41465646 with G as the reference base and with A as a minor allele having a MAF of 0.083; and (5) rs41382844 with G as the reference base and with A as a minor allele having a MAF of 0.105 (see Table 7).

Of the 35 patients initially tested (Group 1), hair follicles from 21 patients exhibited $PGD_2$-mediated growth inhibition while those from the remaining 14 were not affected in their growth by $PGD_2$ (Table 4, FIG. 4B). DNA sequencing of the CRTH2/DP-2 gene as well as SNP PCR showed that roughly 70% of the $PGD_2$-sentitive individuals carry all three SNPs: rs545659, rs634681, and rs7167 (shown in red). Fisher's exact test showed that these three SNPs very likely linked to the sensitivity of these patients to $PGD_2$ inhibition (FIG. 4C).

Subsequently, 88 new samples were collected, and of these, 65 donors (Group 2) had usable culture data. Of the 65 patients tested in Group 2, hair follicles from 31 patients exhibited $PGD_2$-mediated growth inhibition while those from the remaining 34 were not affected in their growth by $PGD_2$ (Tables 5 and 6). DNA sequencing of the CRTH2/DP-2 gene as well as SNP PCR showed that, in Group 2, 22/31=70.96% (vs. 66.7% in Group 1) of the $PGD_2$-sentitive individuals carry all three minor alleles for SNPs: rs545659, rs634681, and rs7167 (Table 5). In Group 2, 8/34=23.53% (vs. 28.57% in Group 1) of the $PGD_2$-insentitive individuals carry all three minor alleles for SNPs: rs545659, rs634681, and rs7167 (Table 6). Fisher's exact test showed that these three SNPs very likely linked ($P<0.001$) to the sensitivity of the Group 2 patients to $PGD_2$ inhibition.

When the results from the 100 samples from both Groups 1 and 2 are combined, hair follicles from 52 patients exhibited $PGD_2$-mediated growth inhibition while those from the remaining 48 were not affected in their growth by $PGD_2$. For the 52 $PGD_2$-sentitive individuals, 36/52 (69.23%) carry minor alleles for the three SNPs: rs545659, rs634681, and rs7167, and the remaining 16/52 (30.77%) $PGD_2$-sentitive individuals are homozygous for the major alleles of these three SNPs. For the 48 $PGD_2$-insentitive individuals, only 12/48 (25.0%) carry minor alleles for the three SNPs: rs545659, rs634681, and rs7167, while the remaining 36/48 (75.0%) $PGD_2$-insentitive individuals are homozygous for the major alleles of these three SNPs. Fisher's exact test showed that these three SNPs very likely linked ($P<0.001$) to the sensitivity of the total population of patients to $PGD_2$ inhibition. Table 7 compares the minor allele frequency in the general population to the $PGD_2$-sentitive and $PGD_2$-insentitive individuals.

TABLE 4

Donor information on tested samples

| No. | Age | Gender |
|---|---|---|
| 21 $PGD_2$ Responders | | |
| 1 | 37 | M |
| 2 | 48 | M |
| 3 | 25 | M |
| 4 | 48 | M |
| 7 | 29 | M |
| 19 | 27 | M |
| 23 | 50 | M |
| 29 | 33 | M |
| 38 | unknown | M |
| 44 | 30 | M |
| 45 | 29 | M |
| 43 | 38 | M |
| 49 | 31 | M |
| 54 | 36 | M |
| 57 | 41 | M |
| 58 | 25 | M |
| 59 | 60 | M |
| 60 | 26 | M |
| 62 | 43 | M |
| 66 | 35 | M |
| 67 | 49 | M |
| 14 $PGD_2$ Nonresponders | | |
| 5 | 30 | M |
| 6 | 49 | M |
| 18 | 25 | M |
| 22 | 39 | F |
| 26 | 24 | M |
| 33 | 39 | M |
| 35 | 50 | F |
| 37 | 27 | M |
| 43 | 26 | F |
| 50 | 38 | M |
| 51 | 36 | M |
| 56 | 52 | M |
| 61 | 30 | M |
| 63 | 28 | M |

TABLE 5

PGd2 Sensitive (31)

| Donor ID | Age, Gender, Treatment | SNP Genotype | | | | |
|---|---|---|---|---|---|---|
| | | rs545659 | rs634681 | rs7167 | rs41465646 | rs41382844 |
| 1 | 41 y/o, M, none | C/T | A/G | A/G | G/G | A/A |
| 2 | 36 y/o, M, none | C/T | A/G | A/G | G/G | A/A |
| 8 | 41 y/o, F, none | C/T | A/G | A/G | G/G | A/A |
| 9 | 54 y/o, M, none | T/T | G/G | A/A | G/G | A/A |
| 11 | 49 y/o, M, none | C/T | G/G | A/G | G/G | A/A |
| 15 | 31 y/o, M, none | T/T | G/G | A/A | G/G | A/A |
| 19 | 31 y/o, F, none | C/T | A/G | A/G | G/G | A/A |
| 20 | 50 y/o, M, none | T/T | G/G | A/A | G/G | A/C |
| 22 | 47 y/o, M, rogaine | C/C | A/A | G/G | G/G | A/A |
| 29 | 53 y/o, M, none | C/C | A/A | G/G | G/G | A/A |
| *32 | 55 y/o, M, propecia | C/T | A/G | A/G | G/G | A/C |
| *35 | 49 y/o, M, none | T/T | G/G | A/A | G/G | A/A |
| 45 | 32 y/o, M, rogaine | C/T | A/G | A/G | G/G | A/A |
| 46 | 44 y/o, M, none | C/T | A/G | A/G | G/G | A/A |
| 48 | 49 y/o, M, propecia | C/C | A/A | G/G | G/G | A/A |
| 49 | 30 y/o, M, none | T/T | G/G | A/A | G/G | A/C |
| 50 | 32 y/o, M, rogaine | C/C | A/A | G/G | G/G | A/A |
| 52 | 35 y/o, M, none | C/T | A/G | A/G | G/G | A/A |
| 53 | 48 y/o, M, none | C/T | A/G | A/G | A/G | A/C |

TABLE 5-continued

PGd2 Sensitive (31)

| Donor ID | Age, Gender, Treatment | SNP Genotype | | | | |
|---|---|---|---|---|---|---|
| | | rs545659 | rs634681 | rs7167 | rs41465646 | rs41382844 |
| 54 | 45 y/o, M, none | C/T | A/G | A/G | A/G | A/C |
| 59 | 42 y/o, M | T/T | G/G | A/A | G/G | A/C |
| 62 | 38 y/o, M, none | C/T | A/G | A/G | G/G | A/A |
| 69 | 35 y/o, M, none | T/T | G/G | A/A | A/G | A/C |
| 70 | 24 y/o, none | C/T | A/G | A/G | G/G | A/A |
| 71 | 25 y/o, M, none | T/T | G/G | A/A | A/G | A/A |
| 73 | 47 y/o, M | C/T | A/G | A/G | G/G | A/A |
| 74 | 46 y/o, M, none | C/T | A/G | A/G | G/G | A/A |
| 76 | 45 y/o, M, none | C/T | A/G | A/G | G/G | A/A |
| 77 | 42 y/o, M, propecia | C/T | A/G | A/G | G/G | |
| 78 | 39 y/o, M, none | T/T | G/G | A/A | A/G | A/A |
| 83 | 45 y/o, M, none | C/C | A/A | G/G | G/G | A/A |
| | | C: 22/31 (71.0%) | A: 22/31 (71.0%) | G: 22/31 (71.0%) | A: 4/31 (12.9%) | C: 7/31 (22.6%) |
| | | T: 9/31 (29.0%) | G: 9/31 (29.0%) | A: 9/31 (29.0%) | G: 27/31 (87.1%) | A: 24/31 (77.4%) |

TABLE 6

PGd2 Insensitive (31)

| Donor ID | Age, Gender, Treatment | SNP Genotype | | | | |
|---|---|---|---|---|---|---|
| | | rs545659 | rs634681 | rs7167 | rs41465646 | rs41382844 |
| 3 | 53 y/o, M, none | T/T | G/G | A/A | G/G | A/A |
| 4 | 32 y/o, M, none | T/T | G/G | A/A | G/G | A/A |
| 5 | 48 y/o, M, rogaine | C/C | A/A | G/G | G/G | A/C |
| 6 | 35 y/o, M, none | T/T | G/G | A/A | G/G | A/A |
| 7 | 52 y/o, M, none | C/T | A/G | A/G | G/G | A/A |
| 10 | 42 y/o, M, none | T/T | G/G | A/A | A/G | A/C |
| 13 | 32 y/o, F, none | T/T | G/G | A/A | A/A | C/C |
| 14 | 21 y/o, M, rogaine | T/T | G/G | A/A | G/G | A/A |
| 16 | 26 y/o, M, propecia | T/T | G/G | A/A | A/G | A/C |
| 17 | 51 y/o, F, none | T/T | G/G | A/A | G/G | A/A |
| 18 | 43 y/o, M, rogaine | T/T | G/G | A/A | G/G | A/A |
| 23 | 35 y/o, M, none | C/T | A/G | A/G | G/G | |
| 24 | 62 y/o, M, none | T/T | G/G | A/A | A/G | A/C |
| 25 | 38 y/o, M, none | C/T | A/G | A/G | G/G | A/A |
| 26 | 61 y/o, M, rogaine | T/T | G/G | A/A | G/G | A/A |
| 27 | 57 y/o, M, none | T/T | G/G | A/A | G/G | A/A |
| 28 | 31 y/o, M, propecia | C/C | A/A | G/G | G/G | A/A |
| 31 | 42 y/o, M, rogaine | T/T | G/G | A/A | A/G | A/C |
| 33 | 56 y/o, M, none | T/T | G/G | A/A | A/A | C/C |
| 34 | 51 y/o, M, rogaine | T/T | G/G | A/A | G/G | A/A |
| 37 | 57 y/o, M, rogaine | T/T | G/G | A/A | G/G | A/A |
| 38 | 42 y/o, M, propecia | T/T | G/G | A/A | G/G | A/A |
| 39 | 63 y/o, M, none | T/T | G/G | A/A | G/G | A/A |
| 47 | 33 y/o, M, none | T/T | G/G | A/A | G/G | A/A |
| 58 | 23 y/o, M, none | T/T | G/G | A/A | G/G | A/A |
| 61 | 52 y/o, F | T/T | G/G | A/A | G/G | A/A |
| 64 | 47 y/o, M, none | T/T | G/G | A/A | A/G | A/C |
| 68 | 36 y/o, M, propecia | T/T | G/G | A/A | G/G | A/A |
| 81 | 30 y/o, M, rogaine, propecia | T/T | G/G | A/A | G/G | A/C |
| 82 | 57 y/o, M, rogaine | C/T | A/G | A/G | G/G | A/A |
| 84 | 25 y/o, M, propecia | C/T | A/G | A/G | G/G | A/A |
| 85 | 63 y/o, M, none | C/T | A/G | A/G | G/G | A/A |
| 86 | 37 y/o, M, none | T/T | G/G | A/A | G/G | A/A |
| 87 | 57 y/o, M, none | T/T | G/G | A/A | G/G | A/A |
| | | C: 8/34 (23.5%) | A: 8/34 (23.5%) | G: 8/34 (23.5%) | A: 7/34 (20.6%) | C: 9/34 (26.5%) |
| | | T: 26/34 (76.5%) | G: 26/34 (76.5%) | A: 26/34 (76.5%) | G: 27/34 (79.6%) | A: 25/34 (73.5%) |

TABLE 7

MINOR ALLELE FREQUENCY IN GENERAL POPULATION VERSUS DONORS

| SNP | UCSC database | NCBI database | PGD2 sensitive donors | PGD2 insensitive donors |
|---|---|---|---|---|
| rs545659 | 0.3291 | 0.3419 | 0.6923 | 0.25 |
| rs634681 | 0.3299 | 0.3403 | 0.6923 | 0.25 |
| rs7167 | 0.3293 | 0.3415 | 0.6923 | 0.25 |
| rs41465646 | 0.0846 | 0.0895 | 0.1923 | 0.3125 |
| rs41382844 | 0.1232 | 0.1232 | 0.2692 | 0.3541 |

In this Example, we have demonstrated that $PGD_2$ inhibits hair follicle growth in a dose-dependent manner by suppressing proliferation and inducing apoptosis of hair follicle epithelial cells. CRTH2/DP-2 antagonists are effective in reversing $PGD_2$'s inhibition on both male and female hair follicles. In this Example, we have demonstrated that $PGD_2$ inhibits hair follicle growth in a dose-dependent manner by suppressing proliferation and inducing apoptosis of hair follicle epithelial cells. In addition, CRTH2/DP-2 antagonists were effective in reversing $PGD_2$'s inhibition on both male and female hair follicles. More specifically, inn animal models, CRTH2/DP-2 antagonists, when applied during the anagen phase directly to the mouse skin, extend the growth phase and promote longer hair shafts.

Hair follicles from a subset of alopecia patients exhibited no growth inhibition by $PGD_2$, indicating the existence of $PGD_2$ responding and non-responding individuals. SNPs were identified in the CRTH2/DP-2 gene that are associated with sensitivity to $PGD_2$ inhibition of hair growth. The existence of $PGD_2$ responding and non-responding individuals with different genotypes in the DP-2 gene indicates that the former group are more responsive to treatment with a DP-2 antagonist to stimulate hair growth and that sensitivity may vary among DP-2 antagonists.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treatment of androgenetic alopecia, baldness or hair loss in a subject that is identified to be likely to be responsive to administration of a DP-2 antagonist that is a selective DP-2 antagonist with respect to DP-1 to stimulate hair growth, comprising:

(i) genotyping single nucleotide polymorphic loci within or flanking the DP-2 gene in a genomic DNA sample obtained from the subject, wherein single nucleotide polymorphic loci rs545659, rs634681, and rs7167 are genotyped;

(ii) determining whether the subject is likely to be responsive to administration of the DP-2 antagonist, based on the genotype detected at each of the loci rs545659, rs634681, and rs7167, wherein the subject is likely to be responsive to administration of the DP-2 antagonist if the subject carries minor alleles for each of the single nucleotide polymorphic loci rs545659, rs634681, and rs7167; and (iii) administering the DP-2 antagonist to the subject who carries minor alleles for each of the single nucleotide polymorphic loci rs545659, rs634681, and rs7167.

2. The method of claim 1, further comprising the step of obtaining the genomic DNA sample from the subject.

3. The method of claim 1, wherein genotyping comprises the step of sequencing the genomic DNA regions that contain the loci.

4. The method of claim 1, wherein genotyping comprises the steps of:

(i) contacting the genomic DNA with one or more detectably labeled oligonucleotides complementary to an allele at said loci; and (ii) detecting the presence or absence of the allele at said loci.

5. The method of claim 2, comprising the step of amplifying the genomic DNA by PCR.

6. The method of claim 5, wherein genotyping comprises the step of sequencing the amplified genomic DNA regions that contain the loci.

7. The method of claim 5, wherein genotyping comprises the steps of:

(i) contacting the amplified genomic DNA with one or more detectably labeled oligonucleotides complementary to an allele at said loci; and (ii) detecting the presence or absence of the allele at said loci.

8. The method of claim 5, wherein the subject has hair loss associated with androgenetic alopecia, discoid lupus erythematosis, congenital hypotrichosis, lichen planopilaris or scarring alopecia.

9. The method of claim 1, wherein the DP-2 antagonist is setipiprant, AM211, ramatroban, an indole acetic acid derivative, a phenyl acetic acid derivative, or a tetrahyrdroquinoline derivative.

* * * * *